(12) United States Patent
Rutenberg et al.

(10) Patent No.: US 8,399,432 B2
(45) Date of Patent: Mar. 19, 2013

(54) COMPOSITIONS AND METHODS OF TREATMENT FOR ALLEVIATING PREMENSTRUAL SYNDROME SYMPTOMS

(75) Inventors: David Rutenberg, Haifa (IL); Rina Perry Faierwerger, Moshav Bat Shlomo (IL)

(73) Assignee: Lipogen Ltd., Haifa (IL)

( * ) Notice: Subject to any disclaimer, the term of this patent is extended or adjusted under 35 U.S.C. 154(b) by 559 days.

(21) Appl. No.: 12/606,975

(22) Filed: Oct. 27, 2009

(65) Prior Publication Data

US 2011/0098249 A1   Apr. 28, 2011

(51) Int. Cl.
  A61K 31/66 (2006.01)
  A61K 9/48 (2006.01)
(52) U.S. Cl. .................................... 514/75; 424/451
(58) Field of Classification Search .............. 424/451; 514/75
  See application file for complete search history.

(56) References Cited

U.S. PATENT DOCUMENTS

| | | | |
|---|---|---|---|
| 5,965,413 A | 10/1999 | Sakai et al. | |
| 6,939,877 B2 | 9/2005 | Webb et al. | |
| 2007/0160659 A1* | 7/2007 | Platt et al. | 424/451 |
| 2010/0298279 A1 | 11/2010 | Bell et al. | |

OTHER PUBLICATIONS

Extended European Search Report in parallel prosecution of patent application No. EP 10154498.9-2123, dated Mar. 24, 2011.
Kidd P M: "Omega-3 DHA and EPA for cognition, behavior, and mood: Clinical findings and structural-functional synergies with cell membrane phospholipids", Alternative Medicine Review 200709 US, vol. 12, No. 3, Sep. 2007 (2007-2009), pp. 207-227, ISSN: 1089-5159.
Ed Silverman; PMDD Is A Real Diagnosis: Yonkers Explains; BulletinHealthcare Briefings; Apr. 25, 2012; htpp://www.pharmalot.com/2012/04/pmdd-is-a-real-diagnosis-yonkers-explains/.
C. N. Epperson, M.D., et al; Premenstrual Dysphoric Disorder: Evidence for a New Category for DSM-5; NIH Public Access; Am J Psychiatry. May 1, 2012; 169(5): 465-467.
Premenstrual dysphoric disorder; Wikipedia, the free encyclopedia; last modified on Nov. 13, 2012; http://en.wikipedia.org/wiki/Premenstrual_dysphoric_disorder.

* cited by examiner

*Primary Examiner* — San-Ming Hui
(74) *Attorney, Agent, or Firm* — Reuven K. Mouallem; FlashPoint IP Ltd.

(57) ABSTRACT

The present invention discloses pharmaceutical/nutritional compositions for alleviating symptoms associated with premenstrual syndrome (PMS) and methods of treatment for PMS using such pharmaceutical/nutritional composition including: at least 2% (w/w) phosphatidyl-L-serine, or salts thereof, out of a total composition, as an effective ingredient, wherein: the phosphatidyl-L-serine has a structural fatty-acid chain derived from at least one raw material lecithin. Preferably, the phosphatidyl-L-serine is produced by enzymatic reaction of at least one raw material lecithin with phospholipase-D; at least one raw material lecithin is selected from the group consisting of: a vegetal lecithin and a non-vegetal lecithin; and the phospholipase-D is selected from the group consisting of: vegetal phospholipase-D, bacterial-originated enzyme phospholipase-D, and a combination of vegetal phospholipase-D and bacterial-originated enzyme phospholipase-D. Preferably, the structural fatty-acid chain is a saturated, hydrogenated fatty-acid chain. Preferably, the phosphatidyl-L-serine is derived from a dairy lecithin.

11 Claims, No Drawings

COMPOSITIONS AND METHODS OF TREATMENT FOR ALLEVIATING PREMENSTRUAL SYNDROME SYMPTOMS

FIELD AND BACKGROUND OF THE INVENTION

The present invention relates to compositions for alleviating symptoms associated with premenstrual syndrome (PMS) and methods of treatment for PMS using such compositions.

The U.S. Department of Health and Human Services, Office on Women's Health, summarizes that PMS is a group of symptoms linked to the menstrual cycle. PMS symptoms occur in the week or two weeks prior to menstruation. The symptoms usually disappear after menstruation starts. PMS can affect menstruating women of any age, and is different for each woman. PMS may be just a monthly bother, or it may be so severe that it makes it hard to even get through the clay. Up to 80% of women experience some symptoms of PMS. The causes of PMS are not clear, and are linked to hormonal changes during the menstrual cycle. Stress and emotional problems do not seem to cause PMS.

It would be desirable to have compositions for alleviating symptoms associated with PMS and methods of treatment for PMS using such compositions.

SUMMARY OF THE INVENTION

It is the purpose of the present invention to provide compositions for alleviating symptoms associated with PMS and methods of treatment for PMS using such compositions.

Embodiments of the present invention provide compositions, for decreasing PMS symptoms, including phosphatidyl-L-serine, either obtained from dairy raw material (e.g. milk lecithin), or produced by an enzymatic conversion utilizing phospholipase-D of raw material lecithin (i.e. mixture of phospholipids) selected from vegetal lecithin (e.g. soybean lecithin, rapeseed lecithin, and sunflower lecithin), egg yolk lecithin, or marine lecithin (e.g. Krill lecithin and fish lecithin).

Embodiments of the present invention provide compositions including phosphatidyl-L-serine, or the salt thereof, as an effective ingredient, wherein the phosphatidyl-L-serine has a structural fatty-acid chain derived from at least one raw material lecithin (e.g. milk lecithin, vegetal lecithin, egg yolk lecithin, or marine lecithin).

Embodiments of the present invention provide methods of treatment for PMS including intravenous administration or oral administration of such compositions. Such compositions can also include other excipients (e.g. additional phospholipids, lyso-phospholipids, sugars, and proteins) to prepare capsules and granules with improved handling and shelf life. Because of the absence of any safety problem, such compositions can be blended into daily foods and beverages, either in powder or liquid form, or as a hydrogenated substance for use in decreasing PMS symptoms.

Phosphatidyl-L-serine from dairy concentrate is freely sold by commercial companies (e.g. LACPRODAN® PL-20 by Arla Foods). Alternatively, the synthesis of phosphatidyl-L-serine by an enzymatic reaction of a raw material lecithin with phospholipase-D is provided herein as an example of one synthetic route. A raw material lecithin (e.g. phosphatidylcholine and phosphatidylethanolamine) selected from vegetal lecithin, egg yolk lecithin, or marine lecithin is subjected to the process of transphosphatidylation with phospholipase-D (e.g. vegetal phospholipase-D, bacterial-originated enzyme phospholipase-D, and a combination of vegetal phospholipase-D and bacterial-originated enzyme phospholipase-D) in the presence of L-serine and water, thereby substituting the choline group and the ethanolamine group with the serine group to produce the rearranged phosphatidyl-L-serine.

Any commercially-available vegetal lecithin, egg yolk lecithin, or marine to lecithin may be used, with no limitation, as the raw material. Phospholipase-D, for use in the process of enzymatic conversion, may be derived from vegetables (e.g. cabbage and peanuts), bacteria (e.g. actinomyces), or any combination thereof that have an activity on lecithin, hydrogenated lecithin, or lysolecithin in the presence of L-serine and water to produce phosphatidyl-L-serine or lysophosphatidylserine. A specific, detailed process for such enzymatic conversion is known in the prior art (e.g. Eibl, A. and Kovatchev, S., "Preparation of phospholipids analogs by phospholipase-D," *Methods in Enzymology*, Vol. 72, pp. 632-639, 1981).

Therefore, according to the present invention, there is provided for the first time a pharmaceutical/nutritional composition for alleviating symptoms associated with premenstrual syndrome (PMS), the pharmaceutical/nutritional composition including: (a) at least 2% (w/w) phosphatidyl-L-serine, or salts thereof, out of a total composition, as an effective ingredient, wherein: (i) the phosphatidyl-L-serine has a structural fatty-acid chain derived from at least one raw material lecithin.

Preferably, (ii) the phosphatidyl-L-serine is produced by enzymatic reaction of at least one raw material lecithin with phospholipase-D; (iii) at least one raw material lecithin is selected from the group consisting of: a vegetal lecithin and a non-vegetal lecithin; (iv) the vegetal lecithin is selected from the group consisting of: soybean lecithin, sunflower lecithin, and rapeseed lecithin; (v) the non-vegetal lecithin is selected from the group consisting of: egg yolk lecithin and marine lecithin; and (vi) the phospholipase-D is selected from the group consisting of: vegetal phospholipase-D, bacterial-originated enzyme phospholipase-D, and a combination of vegetal phospholipase-D and bacterial-originated enzyme phospholipase-D.

Preferably, (ii) the structural fatty-acid chain is a saturated, hydrogenated fatty-acid chain.

Preferably, (ii) the phosphatidyl-L-serine is derived from a dairy lecithin.

Preferably, the pharmaceutical/nutritional composition further includes: (b) a pharmaceutical excipient.

Preferably, the pharmaceutical/nutritional composition further includes: (b) a nutritional excipient.

According to the present invention, there is provided for the first time a method for alleviating symptoms associated with premenstrual syndrome (PMS) in a subject in need thereof, the method including the step of: (a) administering to the subject an effective amount of a pharmaceutical/nutritional composition including: (i) at least 2% (w/w) phosphatidy-L-serine, or salts thereof, out of a total composition, as an effective ingredient, wherein: (A) the phosphatidyl-L-serine has a structural fatty-acid chain derived from at least one raw material lecithin.

Preferably, (B) the phosphatidyl-L-serine is produced by enzymatic reaction of at least one raw material lecithin with phospholipase-D; (C) at least one raw material lecithin is selected from the group consisting of: a vegetal lecithin and a non-vegetal lecithin; (D) the vegetal lecithin is selected from the group consisting of: soybean lecithin, sunflower lecithin, and rapeseed lecithin; (E) the non-vegetal lecithin is selected from the group consisting of: egg yolk lecithin and marine lecithin; and (F) the phospholipase-D is selected from the group consisting of: vegetal phospholipase-D, bacterial-originated enzyme phospholipase-D, and a combination of vegetal phospholipase-D and bacterial-originated enzyme phospholipase-D.

Preferably, (B) the structural fatty-acid chain is a saturated, hydrogenated fatty-acid chain.

Preferably, (B) the phosphatidyl-L-serine is derived from a dairy lecithin.

Preferably, the pharmaceutical/nutritional composition further includes: (ii) a pharmaceutical excipient.

Preferably, the pharmaceutical/nutritional composition further includes: (ii) a nutritional excipient.

Preferably, the step of administering is performed by delivering the effective amount of the pharmaceutical/nutritional composition to the subject in a multi-part regimen.

Preferably, the step of administering is performed by intravenously delivering the effective amount of the pharmaceutical/nutritional composition to the subject.

Preferably, the step of administering is performed by orally delivering the effective amount of the pharmaceutical/nutritional composition to the subject.

These and further embodiments will be apparent from the detailed description and examples that follow.

DESCRIPTION OF THE PREFERRED EMBODIMENTS

The present invention relates to compositions for alleviating symptoms associated with PMS and methods of treatment for PMS using such compositions. The principles and operation for such compositions and methods, according to the present invention, may be better understood with reference to the accompanying description. Exemplary embodiments of the present invention are detailed below in the following three examples of the synthetic processes used to produce the compositions.

EXAMPLE 1-1

Using soybean lecithin as the raw material, phosphatidyl-L-serine is produced by the following process:

Soybean lecithin (50 g. of Epikuron 135; Cargill, Texturizing Solutions Deutschland GmbH & Co. KG) and soybean oil (10 g.) were placed in a 300-ml. vial, followed by the addition of ethyl acetate (50 ml.) for solubilization. A solution (20 ml.) of 0.30 g/ml L-serine dissolved in 0.1M sodium phosphate buffer, pH 7.0, was added to the resulting solution for thorough blending. A solution of 500 U/ml. phospholipase-D from cabbage was then added to the mixture solution for reaction at 25° C. for 5 hrs. while stirring.

In order to inactive the enzyme in the reaction solution, the vial containing the reaction solution was immersed in hot water. Subsequently, the reaction solution was cooled in ice to separate the solution into two layers, which were then left to stand for 30 minutes. The upper layer was then discarded. The remaining lower layer was extracted in chloroform, which was then dried under reduced pressure.

EXAMPLE 1-2

Using egg yolk lecithin (DS-PL95E; Doosan Corp., Venture BG Biotech BU, Korea) as the substrate, rearranged phosphatidyl-L-serine and phosphatidic acid were produced using the method described in Example 1-1.

EXAMPLE 2-1

Soybean lecithin (Epikuron 135; Cargill, Texturizing Solutions Deutschland GmbH & Co. KG) was processed for hydrogenation. Using the hydrogenated soybean lecithin as the substrate, phosphatidyl-L-serine was produced using the method described in Example 1-1.

EXAMPLE 2-2

The soybean lecithin-derived phosphatidyl-L-serine (1 g.) produced in Example 1-1 was solubilized in a mixture solution of n-hexane (15 g.) and ethanol (3 g.). Adding 10% palladium carbon (0.15 g.) to the solution, the resulting solution was processed for hydrogenation for about 5 hrs. while stirring under the conditions of room temperature and ambient pressure.

EXAMPLE 3

The effect of alleviating PMS symptoms via oral administration was investigated in the following experiment. Phosphatidyl-L-serine was prepared by Lipogen Products (9000) Ltd. via the process of enzymatic reaction from a substrate soybean lecithin using the method described in Example 1-1. Five female volunteers who normally suffer from PMS symptoms received 100 mg. of phosphatidyl-L-serine three times per day from three weeks before the expected monthly menstruation until the commencement of menstruation. The results are presented in Table 1.

TABLE 1

The effect of alleviating PMS symptoms using a phosphatidyl-L-serine treatment in an initial treatment regimen experiment.

| Subject age | PMS physical symptoms with treatment | PMS behavioral symptoms with treatment | Cumulative PMS symptoms with treatment |
| --- | --- | --- | --- |
| 27 | 0 | + | + |
| 35 | ++ | ++ | ++ |
| 32 | ++ | ++ | ++ |
| 29 | + | + | + |
| 34 | ++ | + | ++ |

The PMS symptom scale used in Table 1 was based on an assessment by the subject. Examples of the PMS physical symptoms include acne, breast swelling and tenderness, feeling tired, having trouble sleeping, upset stomach, bloating, constipation, diarrhea, headache, backache, appetite changes, food cravings, and joint and muscle pain. The PMS behavioral symptoms include any changes that the subjects noticed in everyday behavior. The results correlate to the following subjective ranking: "0"=no improvement, "+"=slight improvement, and "++"=large improvement. As indicated in Table 1, a significant improvement was observed in all five participants, irrespective of age.

EXAMPLE 4

The effect of alleviating PMS symptoms via oral administration was further investigated in the following experiment. Phosphatidyl-L-serine was prepared by Lipogen Products (9000) Ltd. via the process of enzymatic reaction from a substrate soybean lecithin using the method described in Example 1-1. After two menstruation cycles after the menstruation date of the test in Example 3, the same five female volunteers who participated in the test described in Example 3 above all reported that after cessation of the treatment, their usual PMS symptoms reappeared. The above five female volunteers then received 100 mg. of phosphatidyl-L-serine three times per day from three weeks before the expected monthly menstruation until the commencement of menstruation. The results are presented in Table 2.

TABLE 2

The effect of alleviating PMS symptoms using a phosphatidyl-L-serine treatment in a secondary treatment regimen experiment after the re-emergence of symptoms.

| Subject age | PMS physical symptoms with treatment | PMS behavioral symptoms with treatment | Cumulative PMS symptoms with treatment |
|---|---|---|---|
| 27 | + | + | + |
| 35 | ++ | ++ | ++ |
| 32 | ++ | ++ | ++ |
| 29 | + | + | + |
| 34 | ++ | + | ++ |

The PMS symptom scale used in Table 2 was based on an assessment by the subject. Examples of the PMS physical symptoms include acne, breast swelling and tenderness, feeling tired, having trouble sleeping, upset stomach, bloating, constipation, diarrhea, headache, backache, appetite changes, food cravings, and joint and muscle pain. The PMS behavioral symptoms include any changes that the subjects noticed in everyday behavior. The results correlate to the following subjective ranking: "0"=no improvement, "+"=slight improvement, and "++"=large improvement. As indicated in Table 2, a significant improvement was observed in all five participants, irrespective of age.

As described above, the treatment has a prominent effect for alleviating symptoms associated with PMS using compositions including phosphatidyl-L-serine as an effective ingredient either from a dairy raw material (e.g. milk lecithin), or produced by an enzymatic conversion with phospholipase-D in the presence of L-serine and water from at least one raw material lecithin selected from vegetal lecithin (e.g. soybean lecithin, rapeseed lecithin, and sunflower lecithin), egg yolk lecithin, or marine lecithin (e.g. Krill lecithin and fish lecithin). The treatment can be continuously and readily administered with no pain because phosphatidyl-L-serine supplied in the compositions described above is freely ingested. Furthermore, the phosphatidyl-L-serine compositions for alleviating PMS symptoms can be produced at low cost and in large scale by utilizing the enzymatic conversion process.

While the invention has been described with respect to a limited number of embodiments, it will be appreciated that many variations, modifications, and other applications of the invention may be made.

What is claimed is:

1. A method for alleviating symptoms associated with premenstrual syndrome (PMS) in a subject in need thereof, the method comprising the step of:
    (a) administering to the subject an effective amount of a pharmaceutical/nutritional composition including:
    (i) at least 2% (w/w) phosphatidy-L-serine, or salts thereof, out of a total composition, as an effective ingredient, wherein:
    (A) said phosphatidyl-L-serine has a structural fatty-acid chain derived from at least one raw material lecithin.

2. The method of claim 1, wherein:
    (B) said phosphatidyl-L-serine is produced by enzymatic reaction of at least one raw material lecithin with phospholipase-D;
    (C) said at least one raw material lecithin is selected from the group consisting of: a vegetal lecithin and a non-vegetal lecithin;
    (D) said vegetal lecithin is selected from the group consisting of: soybean lecithin, sunflower lecithin, and rapeseed lecithin;
    (E) said non-vegetal lecithin is selected from the group consisting of: egg yolk lecithin and marine lecithin; and
    (F) said phospholipase-D is selected from the group consisting of: vegetal phospholipase-D, bacterial-originated enzyme phospholipase-D, and a combination of vegetal phospholipase-D and bacterial-originated enzyme phospholipase-D.

3. The method of claim 1, wherein:
    (B) said structural fatty-acid chain is a saturated, hydrogenated fatty-acid chain.

4. The method of claim 1, wherein:
    (B) said phosphatidyl-L-serine is derived from a dairy lecithin.

5. The method of claim 1, wherein said pharmaceutical/nutritional composition further includes:
    (ii) a pharmaceutical excipient.

6. The method of claim 1, the pharmaceutical/nutritional composition further includes:
    (ii) a nutritional excipient.

7. The method of claim 1, wherein said step of administering is performed by delivering said effective amount of said pharmaceutical/nutritional composition to the subject in a multi-part regimen.

8. The method of claim 1, wherein said step of administering is performed by intravenously delivering said effective amount of said pharmaceutical/nutritional composition to the subject.

9. The method of claim 1, wherein said step of administering is performed by orally delivering said effective amount of said pharmaceutical/nutritional composition to the subject.

10. The method of claim 1, wherein said effective amount is effective for alleviating representative symptoms associated with PMS.

11. The method of claim 10, wherein said representative symptoms are associated with premenstrual dysphoric disorder (PMDD).

* * * * *